(12) United States Patent
Mimoun

(10) Patent No.: US 6,392,103 B1
(45) Date of Patent: May 21, 2002

(54) ENANTIOSELECTIVE REDUCTION OF KETONES WITH A SILANE AGENT/METAL COMPOUND/CHIRAL LIGAND SYSTEM

(75) Inventor: Hubert Mimoun, Challex (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/485,388

(22) PCT Filed: Sep. 3, 1998

(86) PCT No.: PCT/IB98/01378

§ 371 Date: Feb. 9, 2000

§ 102(e) Date: Feb. 9, 2000

(87) PCT Pub. No.: WO99/12877

PCT Pub. Date: Mar. 18, 1999

(30) Foreign Application Priority Data

Sep. 9, 1997 (CH) ............................................. 2110/97
Apr. 1, 1998 (CH) ............................................. 778/98

(51) Int. Cl.⁷ .......................... C07C 27/00; C07C 29/14
(52) U.S. Cl. ....................................... 568/814; 568/881
(58) Field of Search ................................. 568/881, 814, 568/878, 880, 822, 823, 876

(56) References Cited

U.S. PATENT DOCUMENTS 5,227,538 A   7/1993   Buchwald et al. .......... 568/814
5,831,133 A   11/1998  Mimoun ..................... 568/814

FOREIGN PATENT DOCUMENTS

WO    WO 96/12694    5/1996

OTHER PUBLICATIONS

Carter et al., "Enantioselective Hydrosilylation of Ketones with a Chiral Titanocene Catalyst", *J. Am. Chem. Soc.*, vol. 116, No. 26, pp. 11667–11670 (1994).
Nitzsche et al., "Reduktionen mit Methyl–wasserstoff–polysiloxanen", *Angew. Chem.*, vol. 69, No. 3, p. 96 (1957).

*Primary Examiner*—Samuel Barts
*Assistant Examiner*—Elvis O. Price
(74) *Attorney, Agent, or Firm*—Winston & Strawn

(57) ABSTRACT

A process for the enantioselective reduction of prochiral ketones to chiral alcohols by (a) the reaction of a prochiral ketone with a silane agent, which is present in a stoichiometric quantity, in the presence of a catalyst derived from a Zn, Co or Cd precursor compound and from a chiral amine, imine, alcohol or amino alcohol ligand; (b) the hydrolysis of the siloxane obtained using an appropriate agent; and (c) the separation and purification of the optically active alcohol formed. Polymethylhydrosiloxane (PMHS) is a preferred silane agent, zinc is a preferred metal, and the precursor compound is produced by reacting a salt or complex of the respective metal with the reducing agent. In another embodiment, an appropriate salt of the chosen metal is used directly in the reaction with the chiral ligand to produce the catalytic form after reaction with the ligand. The process enables high enantiomeric excesses (ee) to be obtained in chiral alcohols.

18 Claims, No Drawings

ENANTIOSELECTIVE REDUCTION OF KETONES WITH A SILANE AGENT/METAL COMPOUND/CHIRAL LIGAND SYSTEM

This is the National phase Application of PCT/IB98/01378, filed Sep. 3, 1998.

TECHNICAL FIELD AND PRIOR ART

The present invention relates to the field of organic synthesis. More specifically, it concerns a process for the asymmetric reduction of prochiral ketones to chiral alcohols using as reducing agent a silane agent, preferably polymethylhydro-siloxane (PMHS), and zinc, cobalt or cadmium compounds, together with ligands selected from the group comprising chiral amines, imines, alcohols and amino alcohols.

The enantioselective reduction of ketones to alcohols is a field in which there is considerable scientific activity in view of the potential industrial importance of this reaction. The production of chiral alcohols is of great importance, particularly in the fine chemicals industry, for example in the pharmaceuticals industry, the perfumes and flavourings industry, and the agrochemicals industry, and for the production of insecticides. Research workers are endeavouring to find processes which produce high yields and enantiomeric excesses but which still use metal catalysts and ligands which are readily available at reasonable prices; the same criteria also apply to reducing agents.

In this context, reference should be made to the publications of Buchwald et al, in particular to U.S. Pat. No. 5,227,538, which describes the enantioselective reduction of ketones using silanes in the presence of catalysts selected from the metal compounds in groups 3, 4, 5 and 6 of the periodic table, and from lanthanides and actinides, and, more particularly, from titanium derivatives, the said catalysts being used in the presence of chiral additives such as amines, diamines and diols. These systems are generally not very active and produce moderate enantiomeric excesses, generally below 40%.

In J. Am. Chem. Soc., 1994, 116, 11667, Carter, Schiott, Gutierrez and Buchwald also described the enantioselective reduction of ketones using PMHS in the presence of chiral titanocenes activated by butyllithium, but these systems have the disadvantage of being very expensive and of requiring relatively large quantities of catalyst, namely, of the order of 5%, based on the substrate.

In the context of the present invention, reference is also made to the applicant's international patent application WO 96/12694, which describes the reduction of aldehydes, ketones, esters and lactones using a reducing system comprising a silane derivative and a metal hydride formed from a metal salt or complex and a reducing agent. It is possible to use not only zinc salts but also cadmium, manganese and iron salts as precursors for the production of the metal hydride. According to a preferred embodiment, polymethylhydrosiloxane (PMHS) is used as the silane derivative. This process is not, however, suitable for the production of chiral alcohols.

DESCRIPTION OF THE INVENTION

We have now discovered that it is possible to prepare chiral secondary alcohols of considerable optical purity economically by reducing prochiral ketones using a silane derivative, preferably PMHS, in the presence of zinc, cobalt or cadmium derivatives complexed by chiral ligands such as amino alcohols, alcohols, amines or imines.

The process comprises the following steps:

a) the reaction of a prochiral ketone with an effective amount of a silane agent in the presence of a catalyst derived from a zinc, cobalt or cadmium precursor compound and from a chiral ligand selected from the group consisting of chiral amines, imines, alcohols and amino alcohols;

b) the hydrolysis of the siloxane obtained using an appropriate agent;

c) the separation and purification of the optically active alcohol formed.

The process is characterised, in particular, in that small quantities of the zinc, cobalt or cadmium precursor compound and of ligand can be used. Furthermore, these reactants and catalysts are not expensive and do not require special handling precautions, particularly in terms of protection from moisture and air.

Without wishing to prejudge the reaction mechanism of the process of the invention, it seems likely that the reaction characterising this process can be illustrated by the following diagram, which relates to a preferred embodiment:

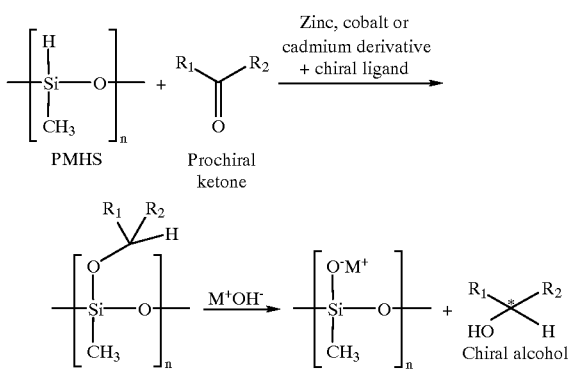

The silane agent used can be a dialkylsilane, a trialkoxysilane, an alkylchlorosilane or a phenylsilane. Dimethylsilane, diethylsilane, trimethoxysilane or triethoxysilane can be cited as examples. According to a preferred embodiment the silane agent used is PMHS or polymethylhydrosiloxane, which has proved to be very effective and is commercially available. Furthermore, unlike other silanes, in a disproportionation reaction PMHS does not form gaseous silanes such as $SiH_4$, a pyrophoric and tear gas which requires special precautions.

Silane agents, which act as the reducing agent in the invention, are used in an effective amount to ensure complete conversion. In general, the amount of silane agent used will be at least the stoichiometric quantity and, according to a preferred embodiment of the invention, the amount of silane agent used will be a slight excess of the order of approximately 10 to 40%, based on the stoichiometric quantity. The reduction reaction according to the invention naturally likewise takes place when the silane agent is used in sub-stoichiometric quantities, but this results in a decrease in conversion. In this case, therefore, the term "effective amount" means an amount of silane agent sufficient to induce reduction of the substrate in an industrially effective manner.

The catalyst according to the invention can be produced in situ in the reaction medium or can be prepared separately. In either case, the catalyst is obtained from a metal precursor compound and a chiral ligand selected from the group comprising amines, imines, amino alcohols and alcohols.

The metal precursor compound used can be zinc, cobalt or cadmium derivatives. The preferred metal compounds of the present invention are zinc compounds, by virtue of their efficacy, ease of handling and non-toxicity.

In an embodiment of the invention, the precursor used is a compound which is prepared in situ from a salt or complex of one of the metals referred to above and from a reducing agent. This embodiment will be used mainly when the metal precursors used are unstable or sensitive, for example, forms which cannot be handled without decomposition taking place. For example, metal hydrides can be prepared by reacting a salt or complex of any respective metal with a reducing agent such as $BH_3$ or a metal borohydride of the formula $M^+BH_4^-$ (M=Li, Na or K) or $M(BH_4)_2$ (M=Mg, Ca or Zn), an alkylborane $MR_nBH_{(4-n)}$ (n=1 to 3, M=alkali metal), an alkoxyborane $(RO)_nBH_{(4-n)}M$ (n=1 to 3, M=alkali metal) or an aluminium hydride such as $AlH_3$, $AlH_nR_{3-n}$, $MAlH_4$, $MAlH_nR_{4-n}$ or $MAlH_n(OR)_{4-n}$ (M=Li, Na or K, n=1 to 3). In the formulae given above, R is an alkyl, cycloalkyl, alkoxy, aryl, aryloxy, alkoxyalkyl, alkoxyaryl, aralkoxy, aralkoyl or alkylaryl group comprising from 1 to 20 carbon atoms. R is preferably a $C_1$ to $C_4$ allyl group. It is also possible to prepare organometallic derivatives by reacting a salt or complex of one of the metals referred to above with an organolithium compound of the formula LiR, an organoaluminium compound of the formula $AlR_3$ or an organomagnesium compound of the formula RMgX (X=Cl, Br or I), R having the meaning defined above. Specific examples include $NaBH_4$, $LiAlH_4$ or $NaAlH_2(OCH_2CH_2OCH_3)_2$ (Vitride®). Reducing agents other than those mentioned above can be used in accordance with common knowledge in the field.

Virtually any salt or complex of the chosen metal can be used in the reaction with the reducing agent to produce the precursor of the active catalyst. In this context, these may include but are not restricted to zinc, cobalt or cadmium halides (fluorides, chlorides, bromides and iodides), carbonates, cyanides, isocyanates, sulphates, phosphates, nitrates, carboxylates (acetates, propionates, 2-ethyl hexanoates, stearates and naphthenates) or alkoxides.

With reference only to the preferred metal of the invention, that is to say zinc, examples of the precursor compounds produced as described above from a zinc salt or complex and a reducing agent are zinc hydride of the formula $ZnH_2$, an organic derivative of the general formula $ZnR_2$, or an organic hydride of the formula ZnHR, in which R is an alkyl, cycloalkyl, alkoxy, aryl, aryloxy, alkoxyalkyl, alkoxyaryl, aralkoxy, aralkoyl or alkylaryl group comprising from 1 to 20 carbon atoms. R is preferably a $C_1$ to $C_4$ alkyl group in this embodiment of the application.

We have also succeeded in developing another embodiment of the process of the present invention in which the precursor used is not a compound produced in situ by reacting a salt or complex of the chosen metal and a reducing agent. Instead, an appropriate salt or complex or organic or hydrogen compound of the chosen metal is used directly as the precursor compound. After reaction with the chiral ligand, the active catalyst is formed without the need for prior activation by a reducing agent. A reducing agent may still be used after or before the reaction between the ligand and the precursor compound, and this may lead to increased yields or enantiomeric excesses.

The metals used in this embodiment are the same metals referred to above, that is to say, zinc, cadmium or cobalt, the preferred metal being zinc. A salt or complex of the general formula $MX_n$ is then used, in which M is selected from the said metals, X is an appropriate anion and n is an integer from 1 to 6. Surprisingly, we found that, in the reduction reaction according to the invention, there is no need to use metal forms which are considered to be highly reactive, such as the hydrides or alkyls which are produced as described above. It has been found that there are a large number of X anions which form salts or complexes of the said general formula $MX_n$ with metals which are useful in the present invention, these salts or complexes being capable of catalysing the enantioselective reduction which forms the subject matter of the invention.

X is preferably an anion selected from a zinc, cobalt or cadmium carboxylate, a $C_1$ to $C_{20}$ alkoxide, β-diketonate, enolate, metallic amide, silylamide, halogen, carbonate or cyanide. In this context, acetates, propionates, butyrates, isobutyrates, isovalerates, diethyl acetates, benzoates, 2-ethyl hexanoates, stearates or naphthenates will preferably be used, as will methoxides, ethoxides, isopropoxides, tert-butoxides, tert-pentoxides, 8-hydroxyquinolinates, optionally substituted acetyl acetonates, tropolonates or fluorides.

It is possible to use not only zinc, cobalt or cadmium salts or complexes but also an organic or hydrogen compound of these metals. A compound of the formula $MX_n$ will be used, in which n is a number from 1 to 6 and X is hydrogen or an organic group such as an alkyl, cycloalkyl, aryl, alkoxyalkyl, alkoxyaryl, aralkoxy, aralkoyl or alkylaryl group comprising from 1 to 20 carbon atoms. R is preferably a $C_1$ to $C_4$ alkyl group or a hydrogen in this embodiment. It is also possible to use a mixed compound of the formula $MX_n$ having at least one X anion as defined above for the zinc, cadmium or cobalt salts or complexes and at least one other X anion formed by an organic group or an atom of hydrogen.

With reference to the preferred metal of the invention, that is to say zinc, the precursor used will be a conventional compound of the general formula $ZnX_2$, in which X has the meaning referred to above. Appropriate examples, according to the invention, of compounds of the alkylzinc, arylzinc or zinc hydride type include dimethylzinc, diethylzinc, dipropylzinc, dibutylzinc, diphenylzinc, $ZnH_2$, ZnH(alkyl), ZnH(aryl), methyl(methoxy)zinc or methyl(phenoxy)zinc, or a derivative of the halogen(alkyl)zinc type.

As mentioned above, the ligands used in the process of the present invention belong to the group comprising chiral amines, imines, alcohols and amino alcohols. It has been found that diamines, diimines, diols and amino alcohols are particularly appropriate for use in the present invention. The aforementioned ligands are known to the person skilled in the art, who is in a position to select from this group the ligand which is most advantageous for the reduction of a specific ketone. Appropriate ligands may include but are not restricted to the families of compounds corresponding to the following formulae:

(I)

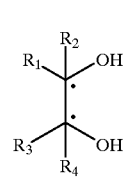

-continued

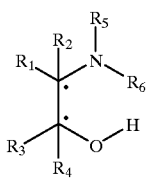
(II)

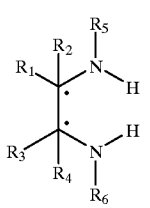
(III)

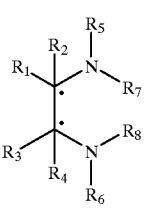
(IV)

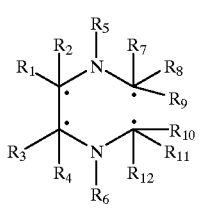
(V)

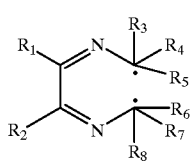
(VI)

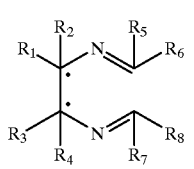
(VII)

In these formulae, the carbon atoms marked with an asterisk and/or the groups $R_1$ to $R_{12}$ may represent stereogenic centres. At least one of these stereogenic centres is responsible for the chirality of ligands (I) to (VII). The groups $R_1$ to $R_{12}$ may be chiral or achiral and are hydrogen atoms or alkyl, cycloalkyl, alkoxy, aryl, aryloxy, alkoxyalkyl, alkoxyaryl, aralkoxy, aralkoyl or alkylaryl substituents comprising from 1 to 20 carbon atoms.

Where the carbon atoms marked with an asterisk do not represent stereogenic centres, the chirality of the ligands is the result of the chirality of at least one of the R groups.

Here the term "stereogenic centre" is understood to mean an atom which is responsible for the chirality of a molecule, such as an asymmetric carbon atom or an atom having atropisomerism.

In a preferred embodiment, a ligand according to one of the formulae (III) to (VII) will be used.

The active catalyst of the invention may be described by the general formula $ZnX_2L^*_n$, when zinc is used. In this formula, X is an anion, an organic group or a hydride as defined above. $L^*$ is one of the ligands of formulae (I) to (VII) referred to above, and n is an integer from 1 to 6. We established that the active catalyst of the invention produced by the reaction of the precursor compound and the respective ligand $L^*$ is a monomeric form of zinc while, in the majority of cases, the precursor compounds are oligo- or polymeric forms.

Zinc chemistry is generally characterised by the need of the metal to attain a coordination number higher than 2, this number being imposed on it by its valence of +2. By oligomerisation or polymerisation, zinc can attain the requisite co-ordination number, generally tetra- or hexacoordination. For this reason, zinc salts or complexes are most frequently oligo- or polymeric. Examples that can be mentioned here are zinc carboxylates and halides.

A class of zinc compounds which are unsaturated in respect of electrons are dialkyl- and diarylzinc compounds. They cannot oligomerise or polymerise, as the alkyl and aryl groups are not capable of acting as bridging ligands. Dialkylzinc and diarylzinc compounds are therefore monomeric and have a linear structure.

We were able to establish that all the compounds mentioned above, that is to say, the oligo- or polymeric zinc compounds and the dialkyl- and diarylzinc compounds display only very slight, if any, activity if they are used for the (non-enantioselective) reduction of ketones. However, when these poly- or oligomeric forms and the compounds of the dialkyl- and diarylzinc type are treated with a ligand of formulae (I) to (VII), which produces a monomeric chiral form, they become highly effective catalysts for the enantioselective reduction of ketones by a silane agent according to the invention.

According to the invention, an oligo- or polymeric zinc precursor salt or complex or a dialkyl- or diarylzinc compound can be used and converted into an active catalyst by treatment with an appropriate complexing agent. We likewise found that it is also possible to use known monomeric zinc complexes or salts, which proved to be active in the process of the invention, while such activity had previously passed completely unnoticed.

The invention also concerns monomeric zinc complexes of the general formula $ZnX_2L^*_n$, in which X is an anion, an organic group or a hydride as defined above, $L^*$ is a ligand of formula (I) to (VII), and n is an integer from 1 to 6. This class of compounds is not known from the prior art. Preferred compounds are those of the general formula referred to above in which X is a carboxylate.

Preferred compounds in this class are Zn(diethyl acetate)$_2$[(S,S)-N-N'-ethylene-bis-(1-phenylethylamine)], Zn(CH$_3$)$_2$[(S,S)-N-N'-ethylene-bis-(1-phenylethyl-amine)] and Zn(C$_2$H$_5$)$_2$[(S,S)-N-N'-ethylene-bis-(1-phenylethylamine)]. The preparation and characteristics of these compounds are described later.

Without wishing to prejudge the reaction mechanism, it is highly likely that, in the case of the other metals which are suitable for use in the present invention, the catalytic form is also a monomeric compound.

Implementation of the process according to the present invention enables yields of the order of 100% and enantiomeric excesses (ee) close to 90% to be obtained. The process of the invention is also very economical, in view of the availability and reasonable prices not only of the silane agents, in particular PMHS, but also of the zinc salts and ligands used. Furthermore, these are used in very small quantities, as will become evident from the following.

The concentration of zinc, based on the substrate, is between 0.1 and 20 mol %, preferably between 0.5 and 5 mol %.

The concentration of ligand, based on the zinc, is between 5 and 200 mol %, preferably between 10 and 100 mol %.

Similar concentrations are used when a cadmium or cobalt compound is used.

One special feature of the reaction according to the invention, which was observed particularly when the zinc derivative was used in conjunction with primary and secondary diimine or diamine ligands, is that the ligand can be used in a sub-stoichiometric quantity, based on the metal, namely in a quantity up to 10 times lower, without the yield or enantiomeric excess being affected. This special feature makes the process according to the invention particularly attractive in economic terms, since the ligand is usually the most expensive constituent of the catalytic system. Its use according to the invention in very small concentrations, namely of the order of 0.1 mol %, based on the substrate, is therefore of considerable value.

The reaction can be carried out at very different temperatures. Temperatures of between −20 and 100° C., preferably between 0 and 60° C., can be mentioned by way of example.

The reaction can be carried out in the absence of solvent or in the presence of a solvent such as an ether, for example methyl-tert-butyl ether, diisopropyl ether, dioxane, tetrahydrofuran, or ethylene glycol dimethyl ether. The reaction can also be carried out in a hydrocarbon solvent such as cyclohexane, toluene, heptane, octane, petroleum ether, xylene or mesitylene.

The process according to the invention can be used for the enantioselective or diastereoselective reduction of ketones.

These ketones may include but are not restricted to acetophenone and its substituted derivatives, hexan-2-one, octan-2-one, nonan-4-one, isophorone, cyclohexyl methyl ketone, α-tetralone, cyclohex-1-en-2-one, cyclopent-1-en-2-one, 2-pentyl cyclopent-1-en-2-one, β-ionone, α-ionone, acetylfuran, dihydro-β-ionone, diketones such as 2,5-hexanedione, α- and β-ketoesters, keto-lactones such as 2-ketopantolactone, keto-armines, keto-amides and keto acids.

MODES FOR CARRYING OUT THE INVENTION

Complexes of the $ZnX_2L_n$ Type Were Prepared as Follows

A. Synthesis of the Zn(diethyl acetate)$_2$[(S,S)-N,N'-ethylene-bis-(1-phenylethyl-amine)]complex This compound was prepared as described below, according to diagram (1):

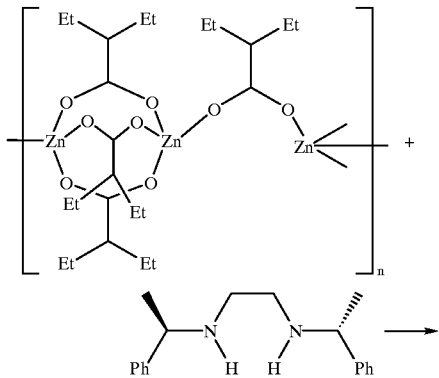

(1)

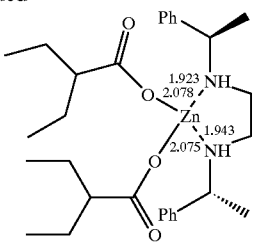

3 g (10 mmol) of zinc diethyl acetate were dissolved in 50 ml of diisopropyl ether, to which 3.1 g (10 mmol) of (S,S,)-N,N'-ethylene-bis-(1-phenylethylamine) ligand were then added. The mixture was stirred at 20° C. and rapidly formed a precipitate which was collected by filtration and then recrystallised in cyclohexane. Yield: 4.2 g (73%). X-ray analysis, based on a single crystal, enabled the structure of this compound to be confirmed.

NMR($^1$H): δ ppm: 0.95 (12H, tt, CH$_3$CH$_2$); 1.55 (6H, d, CH$_3$—CH); 1.6–1.7 (8H, m, CH$_2$—CH); 2.3 (m, 2H, CH—C=O); 2.55–2.8 (m, 4H, CH$_2$—NH); 3.8 (m, 2H, CH—NH); 7.2–7.4 (m, 10H, aromatic);

NMR($^{13}$C): δ ppm: 12.37; 12.42 (q, CH$_3$); 23.36 (q, CH$_3$); 25.99 (t, CH$_2$—); 46.42 (t, CH$_2$—NH); 51.15 (d, CH—); 58.91 (d, CH—); 126–129 (d, d, d); 141.19 (s); 184.9 (s, CO$_2$—).

B. Synthesis of the Zn(CH$_3$)$_2$[(S,S,)-N,N'-ethylene-bis-(1-phenylethylamine)]complex This compound was prepared as described below, according to diagram (2):

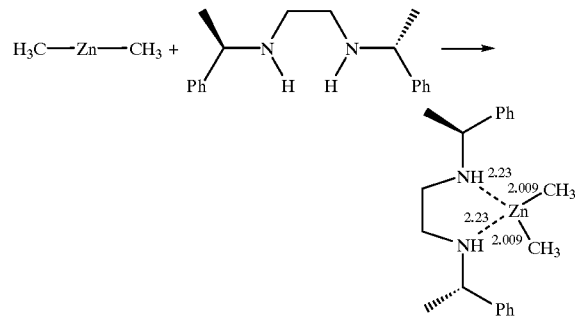

(2)

9.7 mmol of diethylzinc were mixed with 2.5 g of N,N'-bis-(1-(S)-phenylethyl)-1,2-ethylenediamine (9.33 mmol) in 70 ml of toluene. A white precipitate formed immediately. The toluene was evaporated under a vacuum, and the residue was washed with pentane and vacuum-dried. 2.9 g of white crystals were thus obtained (yield 85%).

Elemental analysis: C$_{20}$H$_{30}$N$_2$Zn: weight % calculated: C=66.02; H=8.31; N=7.69. Found: C=66.7; H=8.21; N=7.73.

NMR($^1$H)(CD$_2$Cl$_2$, 25° C., δ ppm): 7.07 (m), 6.76 (m), 3.54 (m, 2H), 1.82 (m, 2 1.63 (m, 2H), 1.39 (d, 6H, J=6.8 Hz), 1.23 (m, 2H), −0.29 (s, 6H).

C. Synthesis of the Zn(C$_2$H$_5$)$_2$[(S,S,)-N,N'-ethylene-bis-(1-phenylethylamine)]Complex This compound was prepared as described below, according to diagram (3):

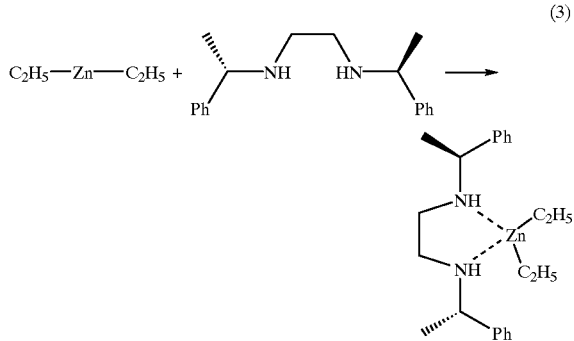

(3)

1.40 g of diethylzinc (11.3 mmol) were mixed with 3 g of N,N'-bis-(1-(S)-phenylethyl)-1,2-ethylenediamine (11.3 mmol) in 50 ml of toluene, and the mixture was stirred for 1 h at 20° C. The toluene was evaporated under a vacuum, and 50 ml of pentane were then added to the residue. The suspension was cooled at −25° C. for 1 h, then filtered and vacuum-dried. 3.16 g of white crystals were thus obtained (yield 71%).

Elemental analysis: $C_{22}H_{34}N_2Zn$: weight % calculated: C=67.42; H=8.74; N=7.15. Found: C=67.51; H=9.02; N=7.06.

IR (Nujol, $v_{max} cm^{-1}$): 3283 (m)

NMR($^1$H)(CD$_2$Cl$_2$, 25° C., δ ppm): 7.36–7.23 (m, 10H), 3.75 (m, 2H), 2.45 (m, 2H), 2.23 (m, 2H), 1.85 (m, 2H), 1.50 (d, 6H, J=6.8 Hz), 1.3 (t, 6H, J=8.1 Hz), −0.04 (m, 4H).

The invention is now described in more detail with the aid of the following examples, in which the temperatures are stated in degrees centigrade, the yields in mol %, and the enantiomeric excesses (ee) by the relationship:

$$\% \, ee = 100 \frac{(R-S)}{(R+S)}$$

in which (R) and (S) are the respective surface areas of the chromatographic peaks of the two enantiomers (R) and (S) in the gaseous phase on a chiral column of the Chirasil® type.

EXAMPLES 1 to 9

Asymmetric Reduction of Acetophenone 10 g of toluene, 1 mmol of a zinc compound such as diethylzinc (Examples 1 to 6 and 9), phenylzinc hydride (Example 7) or zinc hydride (Example 8), and 1 mmol of one of the ligands of the secondary diimine type shown in Table 1 overleaf were added to a 100 ml three-necked flask. The mixture was stirred for 10 min at 20° C., following which 12 g (100 mmol) of acetophenone were added. 6.5 g (100 mmol) of PMHS were then added over a period of 10 minutes, and the solution was stirred continuously for 8 h at 20° C. The complete disappearance of the acetophenone was traced by chromatography. The reaction solution was slowly poured onto an aqueous 30% soda solution (0.15 mol of NaOH). The aqueous phase was decanted, the toluene was evaporated from the organic solution, and the alcohol produced was vacuum-distilled. The enantiomeric excess of the product was determined by chromatographic analysis in the gaseous phase on a chiral column of the Chirasil® type. The Schiff base diimine ligands were prepared by reacting 1 equivalent of commercially available (1R,2R)-(−) diaminocyclohexane with 2 equivalents of 1-naphthaldehyde (Example 1), heliotropin (Example 2), mesitylaldehyde (Example 3) and 2-formylpinane (Example 4) in accordance with Krasik and Alper's description, Tetrahedron, 1994, 50, 4347. The diimine ligands of Examples 5 to 8 were obtained by condensing 2 equivalents of (R)-α-naphthylethylamine (Example 5) or (R)-(α)-phenylethylamine with 1 equivalent of 2,3-butanedione in accordance with Dieck and Dietrich's description, Chem. Ber., 1984, 117, 694. The pyridinyl-imine ligand of Example 9 was prepared by condensing 2-pyridyl carboxaldehyde and (R)-α-phenylethylamine in accordance with Brunner, Reiter and Riepel's method, Chem. Ber., 1984, 117, 1130.

TABLE I

| Example | Zinc compound | Ligand | Alcohol yield (%) | % ee (configuration) |
|---|---|---|---|---|
| 1 | ZnEt$_2$ | | 98 | 75 (S) |
| 2 | ZnEt$_2$ | | 99 | 72 (S) |

TABLE I-continued

| Example | Zinc compound | Ligand | Alcohol yield (%) | % ee (configuration) |
|---|---|---|---|---|
| 3 | $ZnEt_2$ | (structure) | 96 | 70 (S) |
| 4 | $ZnEt_2$ | (structure) | 93 | 53 (S) |
| 5 | $ZnEt_2$ | (structure) | 98 | 56 (S) |
| 6 | $ZnEt_2$ | (structure) | 97 | 48 (S) |
| 7 | PhZnH·Py | (structure) | 95 | 49 (S) |
| 8 | $ZnH_2$ | (structure) | 96 | 48 (S) |
| 9 | $ZnEt_2$ | (structure) | 95 | 35 (S) |

Et = ethyl
Ph = phenyl
Py = pyridine

EXAMPLES 10 to 18
Asymmetric Reduction of Acetophenone

The procedure was the same as in Examples 1 to 9, using diethylzinc (1 mmol) as catalyst and one of the secondary diamine ligands listed in Table II overleaf as ligand (1 mmol). After the mixture had been stirred at 20° C. for 12 hours, hydrolysis was carried out with a 30% excess of soda, and a mixture of the (R) and (S) isomers of the corresponding alcohol was recovered, these isomers being present in the quantities indicated in Table II N,N'-bis-(1-(S)-phenylethyl)-1,2-ethylenediamine (1 mmol), the formula of which is given in Example 11 of Table II, was prepared from 1,2-dichloroethane and (S)-α-phenylethylamine in accordance with Hulst, de Vries and Feringa's method, Tetrahedron: Asymmetry, 1994, 5, 699. The other secondary diamines were prepared by reducing the corresponding diimines using sodium borohydride in a mixture of toluene and methanol (see Corey, Jardine, Yuen and Connell, J. Am. Chem. Soc., 1989, 111, 9243) or by hydrogen gas in the presence of an Adam's $PtO_2$ platinum oxide catalyst (see Alexakis, Mutti and Mangeney, J. Org. Chem., 1992, 57, 1224). These examples show that chiral secondary diamines are particularly appropriate ligands for the enantioselective reduction of acetophenone, producing quasi-quantitative chemical yields and ee which may be as high as 88% (see Example 10).

TABLE II

| Example | Zinc compound | Ligand | Alcohol yield (%) | % ee (configuration) |
|---|---|---|---|---|
| 10 | $ZnEt_2$ | | 98 | 88 (S) |
| 11 | $ZnEt_2$ | | 99 | 75 (R) |
| 12 | $ZnEt_2$ | | 96 | 70 (S) |
| 13 | $ZnEt_2$ | | 97 | 63 (S) |
| 14 | $ZnEt_2$ | | 98 | 62 (S) |
| 15 | $ZnEt_2$ | | 97 | 62 (S) |

TABLE II-continued

| Example | Zinc compound | Ligand | Alcohol yield (%) | % ee (configuration) |
|---|---|---|---|---|
| 16 | $ZnEt_2$ | (cyclohexane-1,2-diyl bis(isopropylamine)) | 95 | 52 (S) |
| 17 | $ZnEt_2$ | (N,N'-bis-(1-phenylethyl)-1,2-ethylenediamine) | 96 | 52 (S) |
| 18 | $ZnEt_2$ | (1,2-diphenyl-N,N'-bis(2-methoxyethyl)ethylenediamine) | 95 | 47 (R) |

Et = ethyl

EXAMPLE 19
Asymmetric Reduction of Acetophenone

The procedure was the same as in Example 11, using diethylzinc (1 mmol) as catalyst and N,N'-bis-(1-(S)-phenylethyl)-1,2-ethylenediamine in a quantity five times less, i.e. 0.2 mmol, as ligand. After the mixture had been stirred at 20° C. for 24 hours, hydrolysis was carried out with a 30% excess of soda, and a mixture of methylphenyl-carbinol comprising 88% of the (S) isomer and 12% of the (R) isomer, that is to say, an ee of 74%, was recovered with a yield of 95%. This example shows that the ligand can be used in a sub-catalytic quantity, that is to say, five times less than that of the metal, without affecting the yield or enantiomeric excess.

EXAMPLES 20 to 22
Enantioselective Reduction of Acetophenone

The procedure was the same as in Examples 1 to 9, but the ligand was replaced by one of the chiral tertiary diamines of Table III. The ligand of Example 22, (R,R)-trans-1,2-bis(N-pyrrolidino)cyclohexane, was prepared in accordance with Corey, Sarshar, Azimioaaa, Newbold and Noe's description, J. Am. Chem. Soc., 1996, 7851, from (R,R)-diaminocyclohexane and 1,4-dibromobutane in the presence of triethylanidne. The ligand of Example 20 was prepared in a similar manner, but the dibromobutane was replaced by α-α'-dichloro-o-xylene. The sparteine used in Example 21 is commercially available.

TABLE III

| Example | Zinc compound | Ligand | Alcohol yield (%) | % ee (configuration) |
|---|---|---|---|---|
| 20 | $ZnEt_2$ | (trans-1,2-bis(isoindolin-2-yl)cyclohexane) | 98 | 55 (S) |

TABLE III-continued

| Example | Zinc compound | Ligand | Alcohol yield (%) | % ee (configuration) |
|---|---|---|---|---|
| 21 | ZnEt$_2$ | (structure) | 99 | 17 (S) |
| 22 | ZnEt$_2$ | (structure) | 96 | 17 (S) |

Et = ethyl

EXAMPLE 23
Enantioselective Reduction of Acetophenone

The procedure was the same as in Examples 1 to 9, using acetophenone (100 mmol) as substrate and the isolated complex Zn(C$_2$H$_5$)$_2$[(S,S)-N,N'-ethylene-bis-(1-phenylethylamine)] as catalyst (1 mmol). After the mixture had been stirred at 20° C. for 18 hours, hydrolysis was carried out with a 30% excess of soda, and a mixture of methylphenylcarbinol comprising 89% of the (R) enantiomer and 11% of the (S) enantiomer, that is to say, an ee of 78%, was recovered with a yield of 95%.

EXAMPLE 24
Enantioselective Reduction of Acetophenone

The procedure was the same as in Examples 1 to 9, using acetophenone (100 mmol) as substrate and the isolated complex Zn(diethyl acetate)$_2$[(S,S)-N,N'-ethylene-bis-(1-phenylethylamine)] (1 mmol) as catalyst. After the mixture had been stirred at 60° C. for 8 hours, hydrolysis was carried out with a 30% excess of soda, and a mixture of methylphenylcarbinol comprising 83% of the (R) enantiomer and 17% of the (S) enantiomer, that is to say, an ee of 65%, was recovered with a yield of 95%.

EXAMPLE 25
Enantioselective Reduction of Acetophenone 2.95 g of zinc diethyl acetate (10 mmol) and 2.68 g of (S,S)-N,N'-ethylene-bis-(1-phenylethylamine) (10 mmol) were added to a 500 ml flask and dissolved in 100 ml of toluene to produce the Zn-(diethyl acetate)$_2$[(S,S)-N,N'-ethylene-bis-(1-phenylethylamine)] complex. 2 g of a 70% solution of Vitride® NaAlH$_2$(OCH$_2$CH$_2$OCH$_3$)$_2$ in toluene (12 mnmol) were then added to the complex solution. The evolution of hydrogen was observed, and the mixture was stirred for 30 min. 120 g of acetophenone (1 mol) were added, followed by 70 g of PMHS (1.08 mol). The mixture was stirred for 12 h at 20° C. When the gas- chromatographic analysis indicated that all the acetophenone had been consumed, hydrolysis was carried out with a 30% excess of soda, and a mixture of methylphenylcarbinol comprising 90% of the (R) enantiomer and 10% of the (S) enantiomer, that is to say, an ee of 80%, was recovered with a yield of 95%.

EXAMPLES 26 to 28
Asymmetric Reduction of 2-pentylcyclopent-1-en-3-one

The procedure was the same as in Examples 1 to 9, but using 2-pentylcyclopent-1-en-3-one as substrate; the ligand used in combination with diethylzinc was one of the commercially available chiral amino alcohols shown in Table IV. 2-pentylcyclopent-1-en-3-ol was obtained with good yields and the optical purities shown in Table IV.

TABLE IV

| Example | Zinc compound | Ligand | Alcohol yield (%) | % ee (configuration) |
|---|---|---|---|---|
| 26 | ZnEt$_2$ | (structure) | 98 | 27 |

TABLE IV-continued

| Example | Zinc compound | Ligand | Alcohol yield (%) | % ee (configuration) |
|---|---|---|---|---|
| 27 | ZnEt$_2$ | 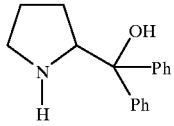 | 69 | 19 |
| 28 | ZnEt$_2$ | 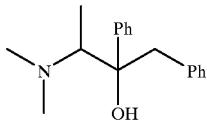 | 76 | 15 |

Et = ethyl
Ph = phenyl

EXAMPLES 29 to 36

Enantioselective Reduction of Various Substrates

The procedure was the same as in Examples 1 to 9, the catalyst used being diethylzinc (1 mol %, based on the substrate) and N,N'-bis-(1-(R)-phenylethyl)-1,2-ethylene-(1 mol %), but the acetophenone was replaced by one of the prochiral ketones or dietones shown in Table V. In all cases, a greater proportion of the (S) enantiomer was obtained, with the ee between 65 and 80%.

TABLE V

| Example | Substrate | Majority product | Alcohol yield (%) | % ee (configuration) |
|---|---|---|---|---|
| 29 | 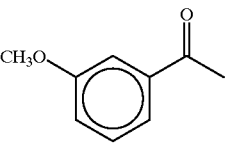 | 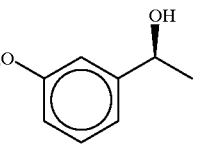 | 98 | 76 (S) |
| 30 | 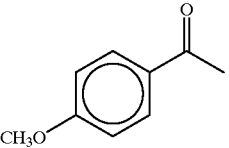 | 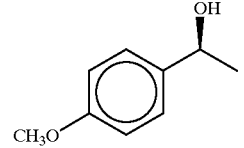 | 99 | 76 (S) |
| 31 | 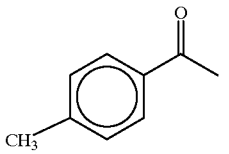 | 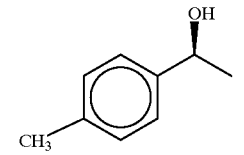 | 97 | 71 (S) |
| 32 | 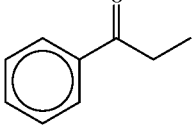 | 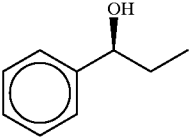 | 95 | 77 (S) |
| 33 | 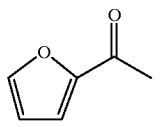 | 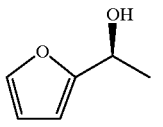 | 99 | 66 (S) |

TABLE V-continued

| Example | Substrate | Majority product | Alcohol yield (%) | % ee (configuration) |
|---|---|---|---|---|
| 34 | 2-acetonaphthone | 1-(2-naphthyl)ethanol | 97 | 80 (S) |
| 35 | 1-acetonaphthone | 1-(1-naphthyl)ethanol | 93 | 75 (S) |
| 36 | α-tetralone | α-tetralol | 90 | 68 (S) |

EXAMPLE 37
Enantioselective Reduction of Acetophenone with a Cadmium Catalyst The procedure was the same as in Examples 1 to 9, using acetophenone (100 mmol) as substrate, cadmium 2-ethyl hexanoate (1 mmol) as catalyst, and as ligand the N,N'-bis(1-(S)-phenylethyl)-1,2-ethylenediamine (1 mmol) of Example 11 of Table II. After the mixture had been stirred at 70° C. for 8 hours, hydrolysis was carried out with a 30% excess of soda, and a mixture of methylphenylcarbinol comprising 82% of the (R) enantiomer and 18% of the (S) enantiomer, that is to say, an ee of 64%, was recovered with a yield of 93%.

EXAMPLE 38
Enantioselective Reduction of Acetophenone with a Cadmium Catalyst The procedure was the same as in Examples 1 to 9, using acetophenone (100 mmol) as substrate, cadmium 2-ethyl hexanoate (1 mmol) as catalyst, and as ligand the N,N'-dibenzyl(S,S)-diphenyl 1,2-ethylenediamine (1 mmol) of Example 10 of Table II. After the mixture had been stirred at 30° C. for 18 hours, hydrolysis was carried out with a 30% excess of soda, and a mixture of methylphenylcarbinol comprising 91% of the (R) enantiomer and 9% of the (S) enantiomer, that is to say, an ee of 82%, was recovered with a yield of 95%.

EXAMPLE 39
Enantioselective Reduction of Acetophenone with a Cobalt Catalyst The procedure was the same as in Examples 1 to 9, using acetophenone (100 mmol) as substrate, cobalt 2-ethyl hexanoate (1 mmol) as catalyst, and as ligand the N,N'-bis(1-(S)-phenylethyl)-1,2-ethylenediamine (1 mmol) of Example 11 of Table II. After the mixture had been stirred at 70° C. for 8 hours, hydrolysis was carried out with a 30% excess of soda, and a mixture of methylphenylcarbinol comprising 80% of the (R) enantiomer and 20% of the (S) enantiomer, that is to say, an ee of 60%, was recovered with a yield of 90%.

What is claimed is:

1. A process for the enantioselective reduction of prochiral ketones to chiral alcohols, the said process comprising the following steps:
   a) the reaction of a prochiral ketone with an effective amount of a silane agent in the presence of a catalyst derived from a zinc, cobalt or cadmium precursor compound and from a chiral ligand selected from the group consisting of amines, imines, alcohols and chiral amino alcohols;
   b) the hydrolysis of the siloxane obtained using an appropriate agent;
   c) the separation and purification of the optically active alcohol formed.

2. A process as claimed in claim 1, characterized in that the precursor compound is prepared in situ by reacting a zinc, cobalt or cadmium complex or salt with a reducing agent.

3. A process as claimed in claim 2, characterized in that the reducing agent is:
   a) a boron hydride of the formula $BH_3$ or $MBH_4$, in which M is Li, Na or K, or of the formula $M(BH_4)_2$, in which M is Mg, Ca or Zn, an alkylborane of the formula $MR_nBH_{(4-n)}$, or an alkoxyborane of the formula $(RO)_nBH_{(4-n)}M$, in which M is an alkali metal, R is an alkyl, cycloalkyl, alkoxy, aryl, aryloxy, alkoxyalkyl, alkoxyaryl, aralkoxy, aralkoyl or alkylaryl group comprising from 1 to 20 carbon atoms, and n is a number from 1 to 3; or
   b) an aluminium hydride of the formula $AlH_3$, $AlH_nR_{3-n}$, $MAlH_4$, $MAlH_nR_{4-n}$ or $MAlH_n(OR)_{4-n}$, in which M, R and n have the meaning given above; or
   c) an agent corresponding to the general formulae LiR, $AlR_3$ or RMgX, in which X is Cl, Br or I, and R has the meaning given above.

4. A process as claimed in claim 3, characterized in that the reducing agent is $NaBH_4$, $LiAlH_4$ or $NaAlH_2(OCH_2CH_2OCH_3)_2$.

5. A process as claimed in claim 1 characterized in that the precursor compound is a zinc compound.

6. A process as claimed in claim 1, characterized in that the zinc, cobalt or cadmium complex or salt is a zinc, cobalt or cadmium fluoride, chloride, bromide, iodide, carbonate, cyanide, isocyanate, sulphate, phosphate, nitrate or carboxylate.

7. A process as claimed in claim 1, characterized in that the precursor compound is a compound selected from a zinc, cobalt or cadmium carboxylate, β-diketonate, enolate, metallic amide, silylamide, halide, carbonate, cyanide, hydride, alkyl, cycloalkyl, alkoxy, aryl, aryloxy, alkoxyalkyl, alkoxyaryl, aralkoxy, aralkoyl or alkylaryl group comprising from 1 to 20 carbon atoms.

8. A process as claimed in claim 7, characterized in that the precursor compound is a zinc compound.

9. A process as claimed in claim 8, characterized in that the precursor compound is a compound of the $ZnX_2$ type, in which X is an acetate, propionate, butyrate, isobutyrate, isovalerate, diethyl acetate, benzoate, 2-ethyl hexanoate, stearate, naphthenate, methoxide, ethoxide, isopropoxide, tert-butoxide, tert-pentoxide, 8-hydroxyquinolinate, substituted or unsubstituted acetyl acetonate, tropolonate or fluoride group, or a compound of the $ZnH_2$, ZnHR, Zn(halogen)R or $ZnR_2$ type, in which R is an alkyl, cycloalkyl, alkoxy, aryl, aryloxy, alkoxyalkyl, alkoxyaryl, aralkoxy, aralkoyl or alkylaryl group comprising from 1 to 20 carbon atoms.

10. A process as claimed in claim 9, characterized in that the zinc compound is selected from dimethylzinc, diethylzinc, dipropylzinc, dibutylzinc, diphenylzinc, methyl(methoxy)zinc or methyl(phenoxy)zinc.

11. A process as claimed in claim 1, characterized in that the silane agent is selected from the group consisting of dialkylsilanes, trialkoxysilanes, alkylchlorosilanes and phenylsilanes.

12. A process as claimed in claim 1, characterized in that the silane agent is polymethylhydrosiloxane (PMHS).

13. A process as claimed in claim 1, characterized in that the chiral ligand is selected from the group consisting of chiral diamines, diimines and amino alcohols.

14. A process as claimed in claim 13, characterized in that the chiral ligand belongs to one of the families of compounds represented by the following formulae:

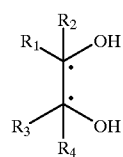

(I)

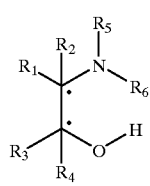

(II)

-continued

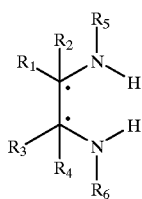

(III)

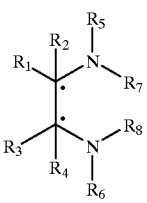

(IV)

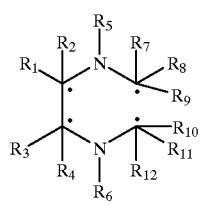

(V)

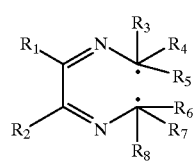

(VI)

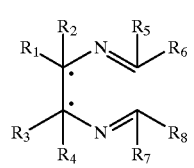

(VII)

in which the stereogenic centres responsible for the chirality of the ligands are either at the corresponding carbon atom marked with an asterisk or at the groups $R_1$ to $R_{12}$, these groups $R_1$ to $R_{12}$ being optionally chiral or achiral and being hydrogen atoms or alkyl, cycloalkyl, alkoxy, aryl, aryloxy, alkoxyalkyl, alkoxyaryl, aralkoxy, aralkoyl or alkylaryl substituents comprising from 1 to 20 carbon atoms.

15. A process as claimed in claim 14, characterized in that the chiral ligand belongs to one of the families of compounds represented by one of the formulae (III) to (VII).

16. A process as claimed in claim 1, characterized in that the concentration of the metal, based on the substrate, is between 0.1 and 20 mol %.

17. A process as claimed in claim 1, characterized in that the concentration of the ligand, based on the metal, is between 5 and 200 mol %.

18. A process as claimed in claim 16 characterized in that metal is zinc.

* * * * *